(12) United States Patent
Aluy et al.

(10) Patent No.: US 12,340,900 B2
(45) Date of Patent: Jun. 24, 2025

(54) METHODS AND SYSTEMS FOR MAXIMIZING OPHTHALMIC MEDICAL DEVICE UPTIME VIA PREDICTIVE HEALTH MONITORING AND PROACTIVE PREVENTATIVE MAINTENANCE

(71) Applicant: Alcon Inc., Fribourg (CH)

(72) Inventors: Nancy Aluy, Irvine, CA (US); John Alfred Campin, Southlake, TX (US); Brian George Green, Newport Coast, CA (US); Mark Andrew Zielke, Lake Forest, CA (US)

(73) Assignee: Alcon Inc., Fribourg (CH)

( * ) Notice: Subject to any disclaimer, the term of this patent is extended or adjusted under 35 U.S.C. 154(b) by 565 days.

(21) Appl. No.: 17/507,668

(22) Filed: Oct. 21, 2021

(65) Prior Publication Data
US 2022/0199241 A1    Jun. 23, 2022

Related U.S. Application Data

(60) Provisional application No. 63/130,333, filed on Dec. 23, 2020.

(51) Int. Cl.
*G16H 40/40* (2018.01)
*A61B 3/00* (2006.01)
(Continued)

(52) U.S. Cl.
CPC ........... *G16H 40/40* (2018.01); *A61B 3/0025* (2013.01); *G05B 23/0283* (2013.01);
(Continued)

(58) Field of Classification Search
CPC ........ G16H 40/40; G16H 10/60; G16H 40/67; G16H 50/20; G16H 50/70; A61B 3/0025;
(Continued)

(56) References Cited

U.S. PATENT DOCUMENTS

2007/0162190 A1   7/2007   Choubey
2010/0076453 A1   3/2010   Morris et al.
(Continued)

FOREIGN PATENT DOCUMENTS

EP    3557589 A1   10/2019
WO    2019035986 A1   2/2019

*Primary Examiner* — Chad A Newton
(74) *Attorney, Agent, or Firm* — PATTERSON + SHERIDAN, LLP

(57) ABSTRACT

Certain aspects of the present disclosure provide techniques for predicting a likelihood of future failure of components in an ophthalmic medical device and performing preventative maintenance on the ophthalmic medical device. An example method generally includes receiving, from an ophthalmic medical device, measurements of one or more operational parameters associated with the ophthalmic medical device. Using one or more models, a future failure of the ophthalmic medical is predicted. The predictions are generated based, at least in part, on the received measurements of the one or more operational parameters. One or more actions are taken to perform preventative maintenance on the ophthalmic medical device based on the predicted future failure of the ophthalmic medical device.

24 Claims, 5 Drawing Sheets

(51) Int. Cl.
*G05B 23/02* (2006.01)
*G06N 20/00* (2019.01)
*G06Q 10/20* (2023.01)
*G06V 40/18* (2022.01)
*G16H 10/60* (2018.01)
*G16H 40/67* (2018.01)
*G16H 50/20* (2018.01)
*G16H 50/70* (2018.01)

(52) U.S. Cl.
CPC .............. *G06N 20/00* (2019.01); *G06Q 10/20* (2013.01); *G06V 40/18* (2022.01); *G16H 10/60* (2018.01); *G16H 40/67* (2018.01); *G16H 50/20* (2018.01); *G16H 50/70* (2018.01)

(58) Field of Classification Search
CPC ...... G05B 23/0283; G05B 2219/24019; G05B 2219/2617; G06N 20/00; G06Q 10/20; G06V 40/18
See application file for complete search history.

(56) References Cited

U.S. PATENT DOCUMENTS

| | | | | |
|---|---|---|---|---|
| 2015/0342723 | A1* | 12/2015 | Abramson | A61F 2/141 |
| | | | | 623/6.64 |
| 2018/0122506 | A1* | 5/2018 | Grantcharov | G16H 50/50 |
| 2019/0260204 | A1* | 8/2019 | Koval | H02J 3/14 |
| 2020/0013501 | A1 | 1/2020 | Page et al. | |
| 2020/0118675 | A1* | 4/2020 | Schriver | G16H 20/17 |
| 2022/0308666 | A1* | 9/2022 | Eash | G06F 3/012 |

* cited by examiner

METHODS AND SYSTEMS FOR MAXIMIZING OPHTHALMIC MEDICAL DEVICE UPTIME VIA PREDICTIVE HEALTH MONITORING AND PROACTIVE PREVENTATIVE MAINTENANCE

CROSS-REFERENCE TO RELATED APPLICATIONS

This application claims priority to and benefit of U.S. Provisional Patent Application No. 63/130,333, filed Dec. 23, 2020, the entire contents of which are incorporated by reference herein in its entirety.

INTRODUCTION

Aspects of the present disclosure relate to ophthalmic medical devices, and more specifically to predicting failures of ophthalmic medical devices at least in part based on data obtained from these devices and performing preventative maintenance on ophthalmic medical devices in response to predicting a future failure of these devices to maximize device uptime.

BACKGROUND

Ophthalmic medical devices generally include devices, consoles, and/or systems that are used to measure or characterize anatomical properties of a patient's eye, to perform surgical procedures on the patient's eye to rectify diagnosed ophthalmic issues, and/or to measure patient's outcome after surgical procedures. These devices include various optical, electrical, and mechanical components that may need to be adjusted or replaced over time. For example, light sources may degrade over time (e.g., may become dimmer over time or require more current to produce the same light intensity) and adversely affect the effectiveness of a device by reducing the amount of detail captured by a device, extending the amount of time needed for light-based treatments to be completed (e.g., laser-based retina reattachment procedures), and the like. In another example, batteries may provide less power over time, and other power source components may generate noisier outputs over time, both of which may adversely affect the operations of an ophthalmic medical device by requiring more frequent battery changes or introducing power instability that may damage mechanical components of the device. In still another example, mechanical devices generally wear over time. Blades generally dull with use, vacuum pumps may not create as effective vacuums over time, gears wear out, motors become less powerful or provide less consistent power, and so on. Further, the performance of the various components in an ophthalmic medical device may degrade differently based on usage patterns, environmental parameters, and the like.

Because the performance of the optical, electrical, or mechanical components of ophthalmic medical devices generally degrades over time, ophthalmic medical devices are typically taken out of service from time to time in order to replace these components and restore the devices to an expected level of performance. In many cases, devices are taken out of service for maintenance when a component breaks or otherwise produces undesirable results, and the broken component may be analyzed to determine the root cause of the failure. However, this may lead to unpredictable availability of ophthalmic medical devices to medical professionals, as a professional may not know or be able to predict when a device will be taken out of service, and may lead to many repeated failures before the root cause of a component failure is discovered.

In some cases, however, preventative maintenance or other remedial actions can be performed to restore the performance level of an ophthalmic medical device back to an expected level of performance. For example, preventative maintenance may allow for components within an ophthalmic medical device to be recalibrated (automatically or manually) to restore the performance of the recalibrated components to an expected performance level. Additionally, preventative maintenance may be used to identify components that are to be replaced before the components break or cause damage to other, related, components within the ophthalmic medical device. Preventative maintenance and other remedial actions, though, may be time consuming processes, and it is generally not efficient to perform preventative maintenance or other remedial actions when not needed. Further, in the field of preventative maintenance as it relates to ophthalmic medical devices, existing techniques for monitoring such devices may not be able to accurately predict when issues with these devices will occur prior to such issues occurring.

Accordingly, techniques are needed for accurately predicting a likelihood of failure and when ophthalmic medical devices or one or more components thereof are likely to fail and for performing preventative maintenance or remedial actions in response to such predictions.

BRIEF SUMMARY

Certain embodiments provide a method for performing preventative maintenance on ophthalmic medical devices based on predictive modeling. The method generally includes receiving, from an ophthalmic medical device, measurements of one or more operational parameters associated with the ophthalmic medical device. Using one or more models, a future failure of the ophthalmic medical device is predicted. The predictions are generated based, at least in part, on the received measurements of the one or more operational parameters. One or more actions may be taken to perform preventative maintenance on the ophthalmic medical device or a component thereof based on the predicted future failure of the ophthalmic medical device.

Certain embodiments provide a method for training a predictive model to predict failure events on an ophthalmic medical device. The method generally includes generating a training data set from a set of measurements of operational parameters associated with the ophthalmic medical device. The training data set generally includes a plurality of records. Each record of the plurality of records identifies a measurement of an operational parameter, a time at which the operational parameter was measured, and a difference between the time at which the operational parameter was measured and a time at which a failure event occurred with respect to the ophthalmic medical device. One or more machine learning models are trained based on the training data set to generate one or more failure predictions in respect of the ophthalmic medical device. The trained one or more machine learning models are deployed to one or more computing systems for use in predicting failures of ophthalmic medical devices and executing remedial or preventative maintenance actions based on the predictions.

Certain embodiments provide a method for performing preventative maintenance on ophthalmic medical devices based on predictive modeling. The method generally includes generating a training data set from a set of measurements of operational parameters associated with an ophthalmic medical device. The training data set may include a plurality of records and each record of the plurality of records identifies: a measurement of an operational parameter, a time at which the operational parameter was measured, and a difference between the time at which the operational parameter was measured and a time at which a failure event occurred with respect to the ophthalmic medical device. One or more machine learning models are trained based on the training data set to generate one or more failure predictions in respect of the ophthalmic medical device. Measurements of one or more operational parameters associated with the ophthalmic medical device are received. A future failure of the ophthalmic medical device is predicted using the one or more trained machine learning models based, at least in part, on the received measurements of the one or more operational parameters. One or more actions to perform preventative maintenance on the component are taken based on the predicted future failure of the ophthalmic medical device.

Aspects of the present disclosure provide means for, apparatus, processors, and computer-readable mediums for performing the methods described herein.

To the accomplishment of the foregoing and related ends, the one or more aspects comprise the features hereinafter fully described and particularly pointed out in the claims. The following description and the appended drawings set forth in detail certain illustrative features of the one or more aspects. These features are indicative, however, of but a few of the various ways in which the principles of various aspects may be employed.

BRIEF DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Figure 1A:
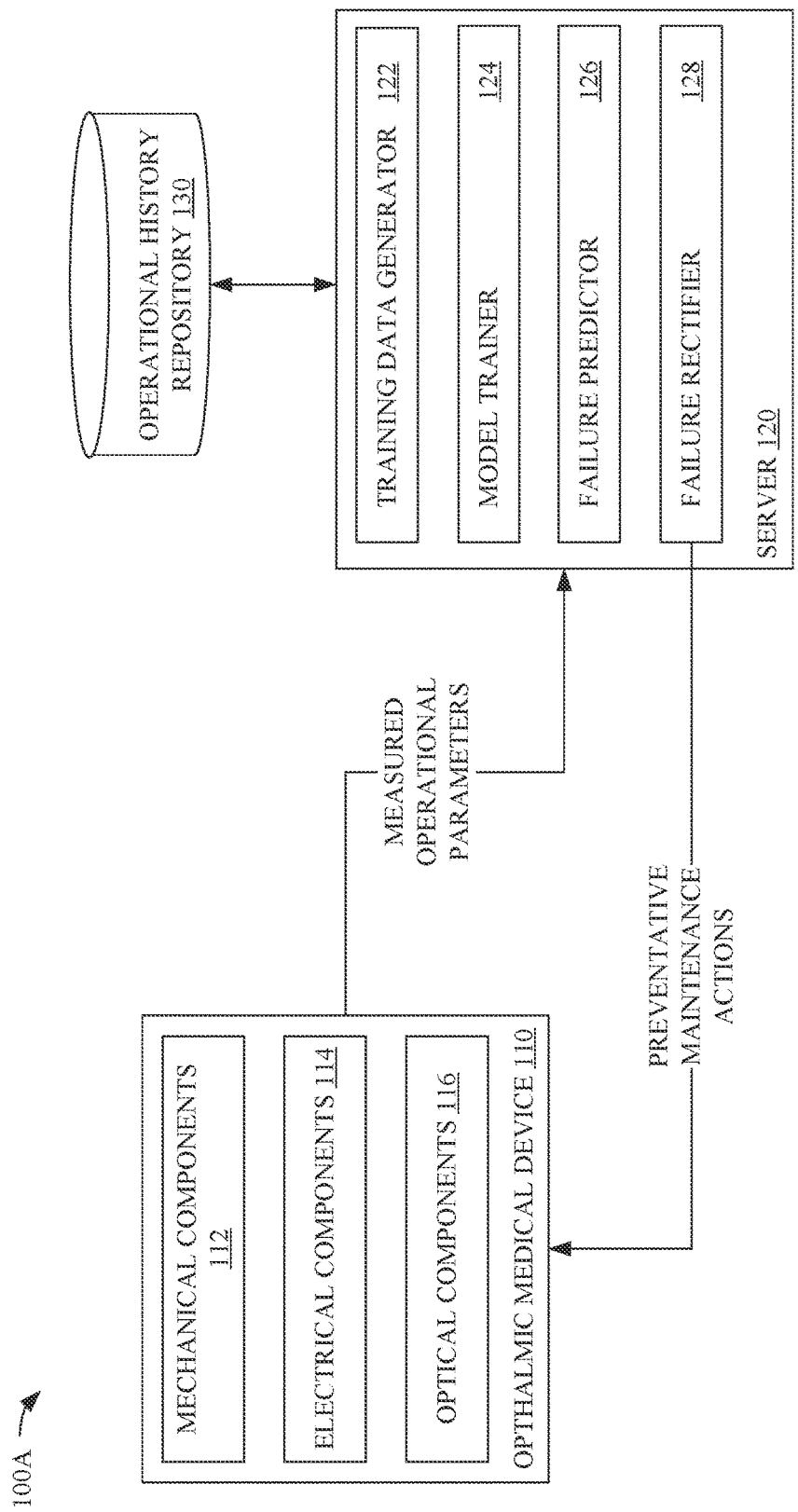
FIGS. 1A-1B depict example environments in which one or more machine learning models are trained and deployed for use in predicting failure of ophthalmic medical devices and/or performing preventative maintenance or other remedial actions based on the predictions, in accordance with certain aspects described herein.

As discussed above, various ophthalmic medical devices (hereinafter "OMDs") may be used in ophthalmology to diagnose and treat conditions or diseases in a patient's eye. These OMDs include, for example, surgical systems and consoles as well as diagnostic and measurement devices and systems. Surgical systems and consoles include systems and consoles used for performing various ophthalmic surgical procedures, such as vitreo-retinal surgical procedures, cataract surgery, LASIK, and/or any other ophthalmic surgical procedures known to one of ordinary skill in the art. Diagnostic and measurement devices and systems include devices and systems used for diagnosing a condition or disease associated with the patient's eye or measuring various anatomical properties of the eye. Examples of diagnostic and measurement devices are refractive diagnostic devices, keratometers, optical coherence tomography (OCT) devices, and/or any other ophthalmic diagnostic and measurement devices and systems known to one of ordinary skill in the art. Each of these OMDs generally includes various components that wear or otherwise degrade over time. Thus, over time, the performance of these OMDs may degrade to the point that the OMDs need to be taken out of service in order to replace worn or broken components.

Taking OMDs out of service generally means that OMDs are unavailable for use by professionals until broken or otherwise degraded components are replaced. Further, a significant amount of time may elapse between the replacement of a broken or degraded component and determination of a root cause for why the component broke or degraded in the first place. Thus, conditions that ultimately caused a component to break or degrade may persist and cause the replaced component to break or degrade similarly, which may ultimately result in additional downtime when the replace component also needs to be replaced.

In some cases, components of an OMD may fail while being used (e.g., during surgery). In such a case, it may be beneficial to proactively take action prior to component failure in order to prevent a situation in which an OMD fails while being used. For example, OMDs may be taken out of service or disable while components in the OMDs are still operational but about to fail.

Aspects of the present disclosure provide techniques for using predictive modeling to predict, given current measured operational parameters of an OMD, a likelihood that one or more components of the OMD are to fail and a time at which such components are likely to fail. With predictive modeling, a large universe of OMD operational data (e.g., and other information that can be used to predict a likelihood, timing, and/or cause of component failure) can be used to accurately predict a likelihood of components failing, a timing of when such components are likely to fail, and/or a cause of such failures. Further, the resulting predictions of a likelihood of failure, a time at which a failure is likely to occur, and/or a cause of a predicted failure can be used as a trigger for performing various remedial or preventative maintenance actions on the OMD, which may extend the operational life of these components. Preventative maintenance actions, as used herein, refers to various actions that may be performed to address conditions in an OMD related to the failure or impending failure of components of the OMD. Such actions may include, for example, adjusting various configuration parameters used in operating the OMD, generating notifications to a user or maintenance personnel identifying the components that are failing or likely to fail, adjusting the operations of the OMD to disable features associated with component that are failing or likely to fail, disabling the OMD until repairs are performed, and the like. By performing these remedial or preventative maintenance operations, aspects of the present disclosure may extend the operational lifespan of components of an OMD and reduce downtime involved in taking OMDs out of service to replace failed components.

Figure 1B:
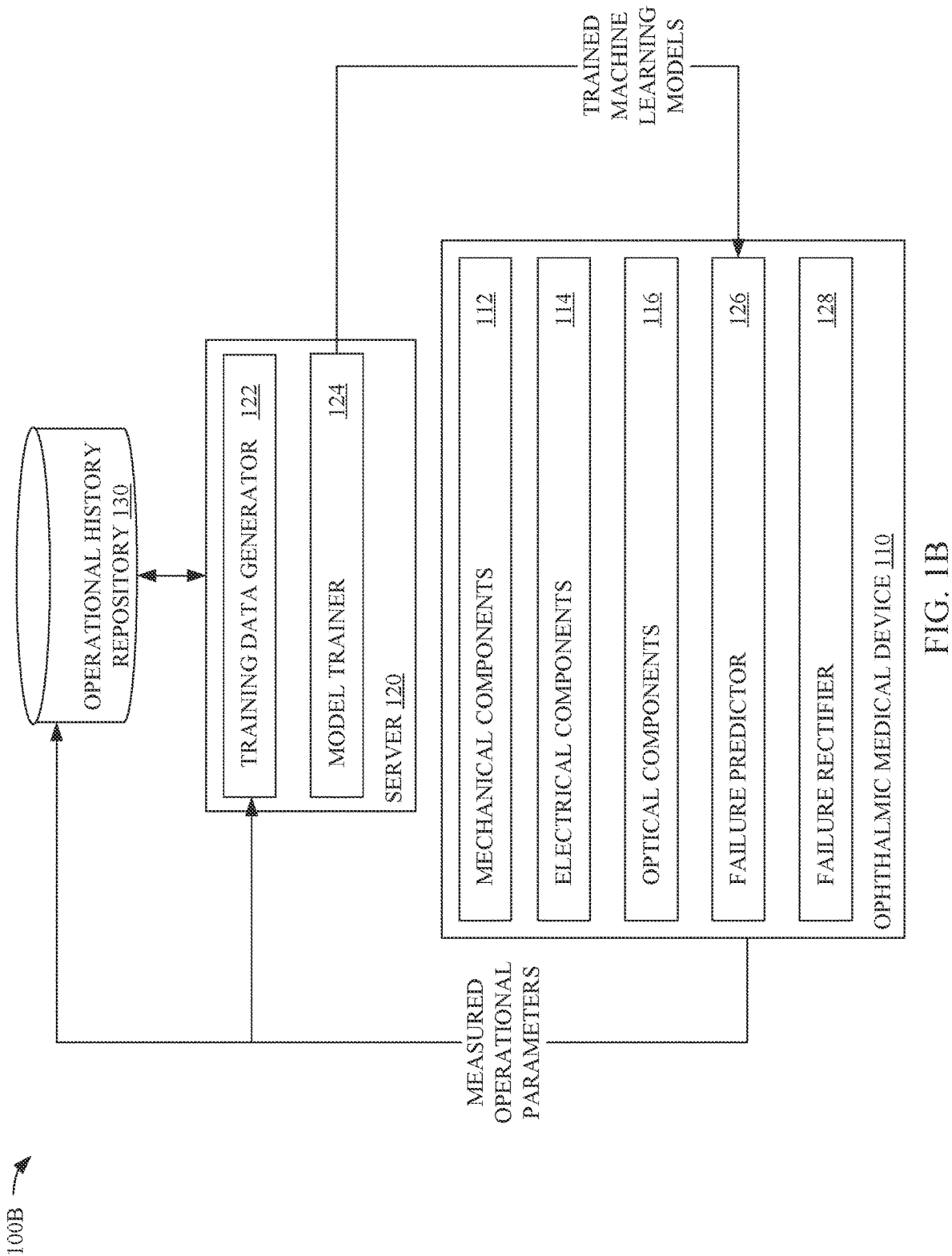

Example Computing Environment for Performing Preventative Maintenance on Ophthalmic Medical Devices Based on Predictive Modeling Various techniques may be used to train and deploy machine learning models that predict a likelihood, timing, and/or root cause of future failure (also referred to herein simply as predicting a failure or predicting a future failure) of one or more components in an OMD. Various deployments are illustrated in FIGS. 1A-1B. For example, FIG. 1A illustrates a deployment in which machine learning models are trained and executed on a remote server that is connected with OMDs being monitored in order to predict a failure and/or cause the execution of preventative maintenance actions in response to a failure prediction. FIG. 1B illustrates a deployment in which machine learning models are trained on a remote server and deployed to OMDs for local failure prediction and/or execution of preventative maintenance actions in response to a failure prediction. It should be recognized, however, that various other techniques for training and deploying machine learning models that predict a future failure of components in an OMD may be contemplated, and that the deployments illustrated in FIGS. 1A-1B are non-limiting illustrative examples.

FIG. 1A illustrates an example computing environment 100A in which an OMD 110 and server 120 are connected via a network in order to train one or more ML models for use in predicting a future failure of one or more components in the OMD 110 and/or executing preventative maintenance actions on the OMD 110 based on the predictions. The ML models, as discussed in further detail herein, may generate the predictions based, at least in part, on operational parameters provided by an OMD with respect to various electrical, optical, and/or mechanical components of the OMD. As used herein, operational parameters generally include parameters indicating an operational state of a corresponding one or more components of an OMD. For example, operational parameters may include input or output voltage or current for electrical components, light intensity generated by lighting components, mechanical operational information (e.g., rotational speed at a motor output shaft or of a device powered by the motor, motor temperature) for mechanical devices, and the like.

OMD 110 is generally representative of various devices that an ophthalmic surgeon can use to diagnose patients and/or perform ophthalmic surgical procedures on such patients. OMD 110 generally includes one or more components that may wear or otherwise degrade over time. For example, as illustrated, OMD 110 includes mechanical components 112, electrical components 114, optical components 116, and/or other types of components. Each of these components may be instrumented with various sensors or other metrology devices that allow for the measurement of various operational parameters of such components. Generally, any number of OMDs may be included in computing environment 100A and generate different sets of operational parameter measurements that may be used as input into one or more ML models that predict a future OMD failure. Each OMD 110 in the computing environment 100A may generate measurements associated with operational parameters and provide the measurements to server 120 and/or operational history repository 140.

In some aspects, OMD 110 may additionally generate and transmit usage pattern data to server 120 for analysis. As used herein, usage pattern data generally refers to information defining historical usage patterns over various time windows. For example, the usage pattern data may include information about a number of times the OMD was used over varying time granularities (e.g., during a day, during specific portions of a day, etc.). This usage pattern data may be indicative of operational conditions leading to additional wear on components of an OMD 110 which may lead to an increased likelihood of failure of the components and correspondingly reductions in the lifespan or maintenance intervals associated with these components. For example, components in an OMD may generate heat each time the OMD is used, and the generated heat may cause the performance of components to degrade, and accumulations of heat may cause additional degradation. Thus, usage pattern data may also be used as an input into a failure prediction system to determine the likelihood and timing of failure.

In some aspects, OMD 110 may include various diagnostic and measurement devices used to generate anatomical measurements of a patient's eye. Generally, an anatomical measurement is a measurement of one or more anatomical properties of a patient's eye, such as white-to-white distance, anterior chamber depth, axial length, or corneal curvature. These anatomical measurements generally fall within a range of expected values, which may be defined as values within two standard deviations of an average measurement. Because roughly 95 percent of measurements are expected to fall within the range of expected values, it is statistically unlikely that more than a certain number of patients will have measurements that are outside the range of expected values. Generally, as discussed in further detail below, patterns of measurements provided by an OMD that are consistently outside the range of expected values may be indicative of an existing or future failure of one or more components of the corresponding OMD.

In some aspects, calibration data, usage pattern data and/or anatomical measurement data discussed above, as well as other information, may be used as inputs into ML models to predict a future failure with respect to components of OMD 110. In cases where calibration data, usage pattern data and/or anatomical measurement data are used as an input into an ML model, an input vector processed by the ML model may include the operational parameter measurements obtained from OMD 110, as well as the calibration data, usage pattern data and/or anatomical measurement data, as discussed in further detail below. In some aspects, the calibration data, usage pattern data and/or anatomical measurement data may be used to determine whether a component of an OMD is of interest for further monitoring or analysis using the ML model(s). For example, as further described below, in certain aspects, the calibration data, usage pattern data and/or anatomical measurement data may trigger the ML model to make predictions of failure of components of OMD 110.

To maintain OMDs 110, calibration operations may be periodically performed on the OMDs. Calibration data generated during calibration operations may include, for example, information defining adjustments to OMDs 110 that are performed in order to bring the OMDs 110 to a known base state. Generally, calibration operations may require larger adjustments to components of the OMDs 110 over time to compensate for additional degradation in the performance characteristics of these components. Calibration operations may be performed periodically or when operational parameters of the components of an OMD 110 degrade to defined thresholds or setpoints. When calibration operations are performed periodically, the amount of the adjustment needed to bring an OMD 110 back to a known base state may be used to determine that an OMD is likely to fail, as discussed in further detail below. Similarly, when calibration operations are performed in response to detecting that measurements of operational parameters have degraded, such as to the defined thresholds or setpoints, a frequency at which such calibration operations are performed may be used to determine that an OMD is likely to fail. For example, if calibrations are being performed more often due to operational parameters degrading more frequently, or if calibrations require larger adjustments to compensate for degradation of components of the OMD, that may indicate that the OMD is likely to fail.

Server 120 is generally representative of a single computing device or cluster of computing devices on which training datasets can be generated and used to train one or more ML models for predicting a future failure of one or more components in an OMD and/or executing preventative maintenance actions on the OMD based on the predictions. Server 120 is communicatively coupled with OMDs 110 and operational history repository 130 (hereinafter "repository 130"), which stores records of historical operational parameters and failure event information (e.g., the cause of a failure, timing information associated with the failure, etc.). In certain aspects, repository 130 may be or include a database server for receiving information from OMDs 110 and/or server 120 and storing the information in corresponding records in a structured and organized manner.

In certain aspects, each record in repository 130 may include information such as an identification of a component of an OMD 110 with which the operational parameters are associated, the operational parameters measured by sensors or other metrology devices associated with the component, a time at which the operational parameters were measured, and a time at which the component eventually failed.

Server 120 uses these records of historical operational parameters and timing information associated with measurements of operational parameters as well as failures of corresponding components in OMDs 110 for use in training ML models to predict a future failure of components in an OMD. More specifically, as illustrated in FIG. 1A, server 120 includes a training data generator 122 (hereinafter "TDG 122"), model trainer 124, failure predictor 126, and failure rectifier 128. TDG 122 retrieves data from repository 130 to generate data sets for use by model trainer 124 to train ML models used by failure predictor 126 to predict a future failure of one or more components in an OMD.

Model trainer 124 includes or refers to one or more machine learning algorithms (referred to hereinafter as "ML algorithms") that are configured to use training datasets to train ML models. In certain embodiments, a trained ML model refers to a function, e.g., with weights and parameters, that is used to generate or predict a future failure of components of an OMD for a given set of inputs. Various ML algorithms may be used to generate different types of outputs for a given set of inputs.

The ML algorithms may generally include a supervised learning algorithm, an unsupervised learning algorithm, and/or a semi-supervised learning algorithm. Unsupervised learning is a type of machine learning algorithm used to draw inferences from datasets consisting of input data without labeled responses. Supervised learning is the machine learning task of learning a function that, for example, maps an input to an output based on example input-output pairs. Supervised learning algorithms, generally, include regression algorithms, classification algorithms, decision trees, neural networks, etc. A description of a data set is provided below.

Once trained and deployed, based on a certain set of inputs, including the operational parameters for a component in an OMD 110 and/or timing information associated with a component failure, the ML models are able to make predictions related to the failure of the component in OMD 110. Generally, predictions made by the ML models may include a likelihood that the component will fail over a given time period and/or a time at which the component is likely to fail. In certain aspects, model trainer 124 trains multiple ML models that are configured to predict failure events for different classes of components in an OMD 110. For example, a first ML model may be configured to predict a future failure for a mechanical component of an OMD based on operational parameters associated with the mechanical component (e.g., input power noise levels, rotational speed, temperature, etc.); a second ML model may be configured to predict a failure for an electrical component of the OMD based on operational parameters associated with the electrical (e.g., input power noise levels, output voltage, output power noise levels, temperature, etc.); a third ML model may be configured to predict a failure for light emitting devices based on operational parameters specific to the light emitting component (e.g., input power noise, input power levels, output luminance, etc.); and so on. In an example, a likelihood of failure could be a general likelihood of failure, such as a 20% chance, 30% chance, etc., that a particular component will fail, that the OMD will fail, etc. In another example, a likelihood of failure could be a likelihood of failure within a particular time period, such as a 20% chance of failure with the next 2 days for a particular component, for the entire OMD, etc.

Each sample in a data set used to train the ML model(s) includes operational parameters specific to a type of device for which the ML model(s) are being trained and/or timing information related to an amount of time elapsed between when the operational parameters were obtained at the OMD 110 and a failure of the relevant component(s) of the OMD. In some cases, each sample in the data set may further include calibration data as well as usage pattern information associated with the measured operational parameters. The usage pattern information may include, for example, a number of times the device was used during a time period between when a previous set of operational parameters was generated and when a current set of measured operational parameters are generated. The usage pattern information may be used to further predict a future failure based on assumptions that heavier usage patterns, or more high intensity usage patterns, are likely to accelerate or otherwise influence the rate at which components in the OMD degrade.

To train the ML model(s), model trainer 124 runs the input data of each sample through the ML model to generate a prediction related to the input data. The prediction, in some aspects, may be a probability distribution over a specified time period (e.g., of n) days, where each day is associated with a probability that the component of the OMD 110 will fail on that day. Generally, because components of the OMD 110 will fail eventually, the total area of the probability distribution will approach 1 (i.e., a 100 percent chance of failure); however, because devices can fail in predictable manners over predicable time periods, the probability distribution may include a plurality of low values and one or more spikes showing that the component is more likely to fail at certain times in the time window. Generally, differences in predicted timing information (i.e., $Y^{\wedge}$ predicted for each sample in the data set) and the actual timing information included in each sample in the data set (i.e., Y included in each sample of the data set) may be calculated and used to train the ML model(s). For example, the predicted timing information may correspond to a predicted number of days until failure of the component, and the actual timing information included in each sample may be the actual number of days elapsed between when the inputs included in each sample were recorded and failure of the component. It should be noted that the timing information discussed above is only an example, and the ML model(s) may be trained to predict $Y^\hat{}$ by learning from actual values of Y that involve other parameters or types of output (e.g., parameters or types of output that do not involve time).

In some aspects, model trainer 124 may train (or refine) the ML models based on an error between the actual timing information and the predicted timing information (i.e., $Y-Y^\hat{}$). In other words, model trainer 124 adjusts the weights in the ML models to minimize the error (or divergence) between the predicted timing information and the actual timing information. As model trainer 124 runs many more samples through the ML model and continues to adjust the weights, the accuracy of the ML models may increase such that the ML models begin to make very accurate predictions with a very low error rate. At that point, the ML models are ready to be deployed to make failure predictions with respect to the various components (e.g., mechanical components 112, electrical components 114, and/or optical components 116) of OMD 110. In the example of FIG. 1A, the trained ML models may be deployed to failure predictor 126 for use in predicting failure for components of OMD 110 based on captured operational parameters, as described in further detail below.

In some aspects, the ML models may be trained using time-series-based algorithms and data sets. For example, the ML models may be trained using long-short-term-memory (LSTM) ML algorithms that are capable of learning timing relationships in data (or other order dependence). Generally, these LSTM models learn functions that map sequences of past observations (i.e., past operational parameters for a component of an OMD 110) to an output observation (i.e., of a probability that the component will fail and a time at which the component will fail). Other ML algorithms, such as recurrent neural networks or other algorithms capable of learning timing relationships between different inputs, may also or alternatively be used to predict a future failure for components of an OMD 110 based on captured operational parameters.

Model trainer 124 may train a single ML model to generate failure predictions for an OMD 110 generally (e.g., to predict a future failure with respect to any component in the OMD 110). In such a case, the data set used to train the single ML model may include operational parameter measurements aggregated across a plurality of monitored components in the OMD 110 and/or timing information related to a failure of the OMD 110. In another example, model trainer 124 may train multiple ML models to generate failure predictions for different components of the OMD 110. The multiple ML models may include a first model trained to generate failure predictions for mechanical components 112, a second model trained to generate failure predictions for electrical components 114, a third model trained to generate failure predictions for optical components 116, and so on. The data sets used to train each of these ML models may include input data that may be used to generate failure predictions for each specific type of component.

Generally, model trainer 124 can re-train the ML model(s) using the dynamic data sets described herein. The data sets may be referred to as dynamic because they may constantly receive and reflect new data points that are gathered from OMD 110 and other OMDs. Re-training may be performed periodically (according to a time schedule), such as after a threshold number of new entries have been added to a historical data set that model trainer 124 uses to train and re-train the ML models, or manually. By re-training the ML models using these dynamic data sets, model trainer 124 can generate ML models that, over time, can make more accurate failure predictions for an OMD or components thereof. The improvements in the accuracy of failure predictions for an OMD may in turn allow for more timely performance of various preventative maintenance actions with respect to one or more components of the OMD 110 and corresponding increases in system uptime.

Failure predictor 126 generally uses captured operational parameters, other information from OMD 110, and the trained ML models to determine whether a component of the OMD is likely to fail. Failure predictor 126 may receive operational parameter measurements and other information from OMD 110 in real time or in periodical batch reports for use in making predictions about component failures for the OMD 110.

Generally, failure predictor 126 can use at least the operational parameter measurements generated by the OMD 110 with respect to the component and various models, such as a priori defined models or the trained ML model(s) applicable to the component, to predict a future failure of components in the OMD (e.g., of a component associated with the operational parameter measurements or upstream or downstream components for which a failure may be indicated by the operational parameter measurements associated with the component). A prediction of a future failure of components in the OMD may include, for example, a likelihood of component failure and/or a likely time at which the component will fail, among other predictions. Generally, a priori defined models need not be trained by model trainer 124 and may be used to determine that a component is failing (e.g., as well as the timing/likelihood thereof) based on known properties of these components. The trained ML models may be used in conjunction with or in place of the a priori defined models to generate failure predictions with respect to a component of OMD 110 (or associated components, as measurements of operational parameters with respect to one component may actually indicate that an upstream or downstream component is actually failing).

As discussed, the ML model(s) may take a set of operational parameter measurements as input and generate a probability distribution as an output. The probability distribution may show the probability of the component failing for each of a plurality of time periods after the operational parameter measurements were generated. For example, over a time window of n days, the probability distribution may show a probability of failure after 1 day, after 2 days, and so on, up to n days. A spike in the probability distribution generally illustrates a most likely time at which the component will fail.

In some aspects, the ML model(s) may take other information as input in conjunction with the set of operational parameter measurements for use in predicting a likelihood of component failure and/or a time at which the component will fail. For example, the ML model(s) may use calibration data, usage pattern information, and/or measurements of anatomical parameters generated by the OMD 110 (or information derived therefrom), in conjunction with the operational parameter measurements, to predict a future failure of components of OMD 110 will fail and/or a time at which the component is likely to fail. The usage pattern information may include, for example, a number of times the OMD 110 was used over a given time period or more granular information about usage over the given time period (e.g., usage during different portions of the given time period). The measurements of anatomical parameters generated over the given time period may be used, for example, to generate information about a proportion of measurements that are outside of the expected range of values for a given anatomical parameter.

In some aspects, a priori defined models may be used to determine whether a component of the OMD 110 is failing based on a priori known values of normal and abnormal operational parameter measurements for the component. For example, an a priori defined model may define normal values of operational parameter measurements in terms of a minimum and maximum value. The maximum value may correspond to a value of an operational parameter measurement at which a failure of the component (or upstream or downstream components) is known to occur. If the received operational parameter measurement for the component of the OMD 110 exceeds this maximum value, failure predictor 126 can determine that the component has failed and can instruct failure rectifier 128 to take one or more actions with respect to the component. In some aspects, a priori defined models may be used initially, and ML models may be trained over time based on captured historical data so that eventually, the trained ML models can be used in place of or in conjunction with the a priori defined models.

In some aspects, various thresholding techniques can be used to determine whether failure predictor 126 is to use the trained ML model(s) to predict a future failure of components of an OMD 110. By using these thresholding techniques, ML models may be used to generate predictions for components of the OMD 110 that are of interest instead of predictions for all components of the OMD 110 regardless of whether components are exhibiting signs of impending failure. Thus, compute resources may be saved by using the ML models to generate predictions only for components that are of interest for additional monitoring.

For example, comparisons of the received operational parameter measurements to expected operational parameter measurements may be used to determine whether the ML models should be used to generate failure predictions for a component of the OMD 110. Generally, each component of an OMD 110 may be associated with predefined normal ranges of operational parameters. For example, a mechanical device may be associated with normal ranges of input currents/voltages, rotational speeds, vibrational measurements, and so on. An electrical device may be associated with normal ranges of output currents/voltages, output noise, heat, and so on. A light-emitting device may be associated with normal ranges of requested input power, output luminance levels, and so on. If OMD 110 reports operational parameters for a component that are within the normal ranges for such a component, failure predictor 126 may determine that the component is operating normally and need not use the ML models predict a future failure of components of the OMD 110, as the components of the OMD are not likely to imminently fail or require closer attention in the near future.

In some aspects, failure predictor 126 may use trend analyses or other statistical analyses to determine whether to use the ML models to generate failure predictions for a component of the OMD 110. As discussed, mechanical, electrical, optical, and light-emitting components in an OMD 110 degrade in performance over time. In some cases, these components may generate consistent operational parameters for some amount of time, then degrade suddenly. In other cases, these components may show a monotonically changing pattern for operational parameters, with more drastic changes occurring as a component reaches the end of its useful life or otherwise approaches a failure state. Based on a priori known degradation characteristics for the operational parameters of a device, failure predictor 126 may examine the operational parameters captured for a component over a time window to detect a trend in the reported operational parameters. If the trend is indicative of imminent failure (e.g., the trend shows a significant change in operational parameters over the time window), failure predictor 126 may determine that components of the OMD 110 should be monitored more closely and thus may use the ML models trained by model trainer 124 to generate failure predictions for the component.

In some aspects, failure predictor 126 may also or alternatively use information about calibration procedures executed on OMDs 110 to determine that components of an OMD should be examined using the ML model(s). Generally, OMDs 110 may execute calibration procedures on a periodic basis (e.g., daily) in order to adjust the components to a known base state. Because the performance of components in an OMD can degrade over time, calibration procedures may gradually require further and further changes in order to adjust the components of the OMD to the known base state. Further, because the performance characteristics of various components may have known patterns, the calibration procedures used to adjust the components of the OMD to a known base state may have patterns that mirror the performance characteristic patterns of the component. Thus, failure predictor 126 may use trend analyses or known ranges of calibration parameters to determine whether to use the ML models to generate failure predictions for the component.

In another example, failure predictor 126 may use anatomical measurements generated by an OMD 110 to determine that components of an OMD 110 should be examined using the ML model(s). As discussed, anatomical measurements generally fall within a known distribution of values. If, however, an OMD 110 consistently generates anatomical measurements that are outside of the known distribution of values, it is more likely that the OMD 110 is failing or likely to fail in the near future. Failure predictor 126 may, for example, determine that an OMD 110 should be examined using the ML model(s) if the number of patients for which the generated anatomical measurements are outside of the known distribution exceeds a threshold percentage of the patients evaluated by the OMD. The anatomical measurements may include, for example, eye tracking information showing patient eye movement recorded while the anatomical measurement was obtained, axial length (i.e., the distance between the anterior cornea and the retina), corneal thickness, anterior chamber depth (i.e., the distance between the anterior cornea and the anterior lens surface), white-to-white diameter (i.e., the distance between the corneal and scleral boundary on either side of the eye), lens thickness, lens curvature, and other anatomical measurements that may be recorded by an OMD during use.

After failure predictor 126 determines that an OMD component is likely to fail and/or identifies a likely time at which the component will fail, failure predictor 126 can provide the prediction and information identifying the failing component to failure rectifier 128 for further processing.

Generally, failure rectifier 128 is configured to perform various preventative maintenance actions with respect to one or more components of the OMD 110. The preventative maintenance actions may vary based on the identity of the component, the current operational parameter measurements recorded for the component, and other information that may be used to determine whether maintenance can be performed on the component remotely.

In some aspects, failure predictor 126 can generate one or more notifications for display to a user of the OMD and/or support personnel who maintain the OMD including information about the predicted future failure of the OMD. These notifications may include, for example, information about the actions taken by failure rectifier 128 in response to the prediction that the component is likely to fail, why the actions were taken (e.g., in response to predictions made based on the values of the operational parameter measurements), and/or other information that may aid in understanding the status of components in the OMD, problems with components in the OMD, and future actions to be taken in response to the prediction that the component is likely to fail.

Failure predictor 126 may be used to perform failure predictions for OMDs located in a wide variety of operating environments and in various geographical regions. Because failure predictor 126 can generate failure predictions for devices in varying operating environments and geographical regions, model trainer 124 and failure predictor 126 can leverage a wide universe of data in training and predicting failures across a wide universe of deployed OMDs. Further, data points obtained from the deployed universe of OMDs may allow for various analyses to be performed based on large data sets. For example, failure predictor 126 may divide the universe of deployed OMDs into a plurality of groups (e.g., regional groups, environmental groups, etc.) to identify failures that are more or less prevalent in these groups. Information about failures that are more prevalent in one group may be provided by failure predictor 126 to engineering groups responsible for particular components of the OMDs to identify root cause(s) of these failures and new designs or procedures with respect to these components that may reduce the prevalence of failures for a particular group of users.

In some aspects, failure rectifier 128 may include a library of programmatic solutions that can be executed to remedy a failure or expected failure of a component of the OMD 110. These programmatic solutions may be associated with, for example, particular types of components and particular sets of operational parameter measurements. Generally, a programmatic solution may include executable code which, when pushed to an OMD 110 for execution, remedies abnormal execution conditions at the OMD 110. These programmatic solutions may include, for example, software patches that control timing of various operations, changes in calibration targets used to adjust the calibration of the OMD 110, and so on. When a match between a programmatic solution and the components and operational parameter measurements reported by the OMD 110 is found, failure rectifier 128 can push the programmatic solution to the OMD 110 for execution.

In some aspects, failure rectifier 128 may determine that a component identified as failing or likely to imminently fail should be replaced in order to remedy a failure or expected failure. Failure rectifier 128 may determine that a component should be replaced based on information identifying that the component is failing due to an electrical or mechanical failure that cannot be compensated by software. For example, failure rectifier 128 may determine that an electrical component should be replaced if progressively higher amounts of power are needed to generate an expected output for the component, as increased power requirements (e.g., and the corresponding increased resistance in the electrical component) may indicate imminent failure that cannot be rectified by software. In another example, failure rectifier 128 may determine that a mechanical component should be replaced if the operational parameter measurements reported for the mechanical component indicate a degradation of performance (e.g., inconsistency in the rotational speed of a motorized device) or indicate that the device has a heartbeat (e.g., is electrically connected with a controller at the OMD 110) but is mechanically inoperative. In such a case, failure rectifier 128 may push one or more instructions to the OMD 110 to disable the OMD until the identified components that have failed or will imminently fail are replaced.

In some aspects, failure rectifier 128 can perform diagnostic tests or other actions with respect to a component on an OMD 110 to further determine if the component is failing or will imminently fail. The diagnostic tests may include instructions that cause the OMD to execute particular operations and provide additional operational parameter measurements to the failure rectifier 128 for analysis. If the additional measurements indicate that the component is failing or likely to fail, failure rectifier 128 can determine that preventative maintenance actions should be performed with respect to the component, as discussed above.

FIG. 1B illustrates another example computing environment 100B in which training and use of the machine learning models to predict a future failure of components in an OMD for use in performing preventative maintenance on the OMD may be performed. As illustrated, computing environment 100B includes a measurement device 110, server 120, and operational history repository 130. In the example illustrated in FIG. 1B, TDG 122 and model trainer 124 execute on server 120, while failure predictor 126 and failure rectifier 128 execute on the OMD 110 using data generated by device component instrumentation associated with mechanical components 112, electrical components 114, and/or optical components 116. The device component instrumentation generally includes various sensors and other metrology devices that can monitor and measure various operational parameters of components on the OMD. These operational parameter measurements, as discussed, may be used, alone or in conjunction with other data, such as calibration data, usage history, or measurements of anatomical parameters for various patients, to predict that a component on the OMD is likely to fail and to identify, based on the prediction, preventative maintenance actions to perform on the OMD to prevent the components from failing.

Figure 2:
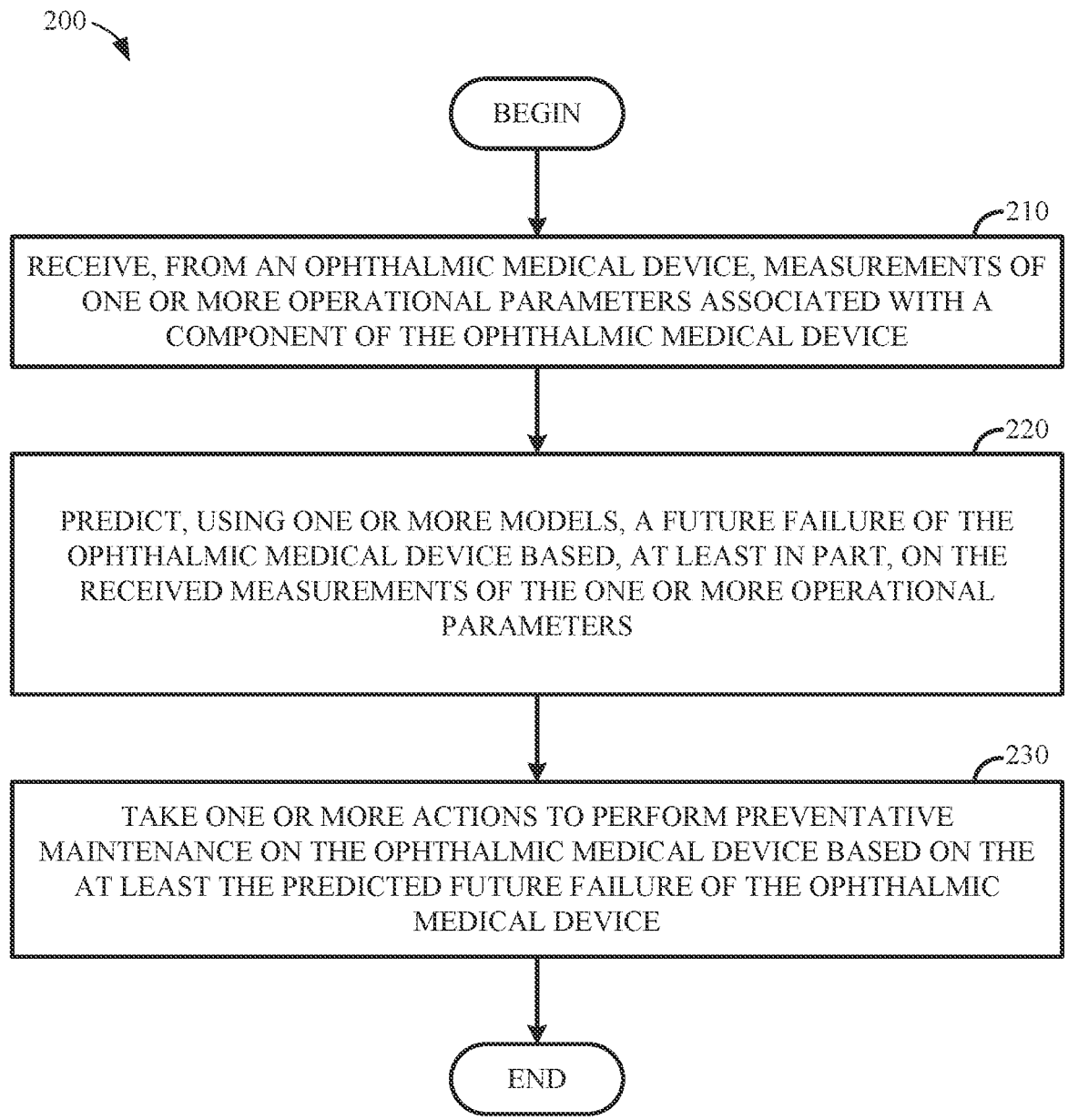
FIG. 2 illustrates example operations that may be performed by computing systems within a networked computing environment to perform preventative maintenance on ophthalmic medical devices based on predictive modeling, in accordance with certain aspects described herein.

Example Methods for Performing Preventative
Maintenance on Ophthalmic Medical Devices
Based on Predictive Modeling FIG. 2 illustrates example operations 200 that may be performed by a computing system to predict future failure of components in an OMD for use in performing preventative maintenance on the OMD. Operations 200 may be performed by one or more of an OMD 110 or a server 120 illustrated in FIGS. 1A-1B.

As illustrated, operations 200 may begin at block 210, where a system receives, from an OMD, measurements of one or more operational parameters associated with a component of the OMD. The measurements may include operational parameter measurements at different times over a period of time. In some cases, the measurements may be received periodically (e.g., according to a heartbeat monitor executing on the OMD or a server at which the measurements are received). For example, the measurements may be received daily, after each time the OMD is used, or according to some other periodicity defined for receiving measurements from the OMD.

At block 220, the system predicts, using one or more models, a likelihood of future failure of the component of the OMD and/or a time at which the component is likely to fail based, at least in part, on the received measurements of the one or more operational parameters. The models may include a priori defined models that identify whether a component is failing based on known values of operational parameter measurements corresponding to normal and abnormal operations or on trained ML models that can predict a future failure of the OMD. Note that identifying whether a component is failing using an a priori model may include predicting a likelihood that the component of the OMD will fail and/or a time at which the component is likely to fail based, at least in part, on the received measurements of the one or more operational parameters. In some cases, to reduce computing resource usage involved in predicting future failure with respect to a component of an OMD, the system can predict a future failure of a component of an OMD in response to determining that other data from the OMD indicates that the component has degraded to a point where predictive modeling and preventative maintenance is warranted.

For example, to determine that predictive modeling is warranted, a system can examine the operational parameter measurements for a component against known specifications for that component. The known specifications may include information, for example, about expected ranges of measured operational parameter values for the component. If the measurements are outside the expected ranges (e.g., by a threshold amount), the system can determine that predictive modeling and preventative maintenance based on the predictive modeling is warranted. In another example, the system can use trend analyses or statistical analyses of the measured optical parameters and historical measurements to determine if the component is exhibiting signs of degraded performance indicative of an impending failure.

In some cases, the system can examine data other than the measured optical parameters or historical measurements for these optical parameters to determine that predictive modeling and preventative maintenance is warranted. For example, the results of calibration tests may be examined to determine whether successively larger amounts of calibration adjustments are being used to calibrate the OMD. Because the use of larger calibration adjustments may indicate that components of an OMD are degrading, calibration adjustments that increase beyond a threshold amount may indicate that a component is failing or likely to fail, and thus that predictive modeling and preventative maintenance is warranted. In another example, the system can examine patient anatomical measurements to determine whether the OMD is consistently generating measurement data that is abnormal relative to a normal distribution of values for an anatomical parameter. If the OMD is consistently generating measurement data that is abnormal, the system can determine that the OMD is performing abnormally and may determine that predictive modeling and preventative maintenance is warranted.

At block 230, the system takes one or more actions to perform preventative maintenance on the component based on the predicted likelihood of failure and/or time at which the component is likely to fail. The one or more actions may include executing code on an OMD that addresses potential failure modes for the OMD, performing additional diagnostic tests on the OMD to determine a further course of action, or disabling the OMD until the failing components are replaced.

Figure 3:
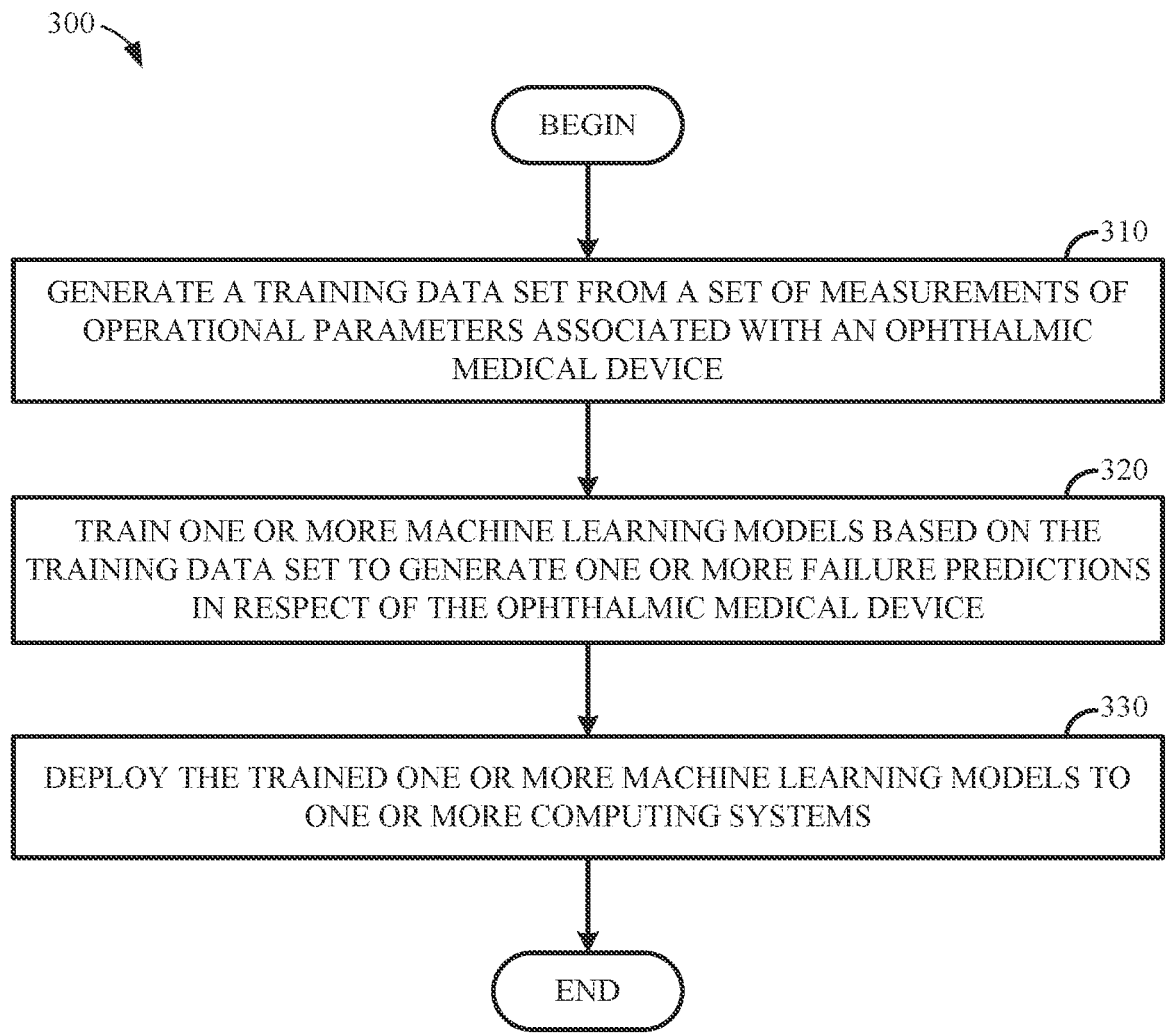
FIG. 3 illustrates example operations that may be performed by one or more computing systems to train one or more machine learning models to predict a likelihood that one or more components of an ophthalmic medical device will fail and/or a time at which the one or more components are likely to fail, in accordance with certain aspects described herein.

FIG. 3 illustrates example operations 300 that may be performed by a system to train machine learning models to predict a future failure of components in an OMD for use in performing preventative maintenance on the OMD. Operations 300 may be performed, for example, by server 120 illustrated in FIGS. 1A-1B.

As illustrated, operations 300 begin at block 310, where the system generates a training data set from a set of operational parameter measurements associated with an OMD. The data set may, in some aspects, include measured operational parameters for various components of the OMD and/or timing information associated with a time at which the measurements were obtained at the OMD and a time at which the OMD failed. Generating the training data set may entail generating different training data sets for different components or classes of components for the OMD, as different components or classes of components may have different parameters that indicate a likelihood of future failure.

At block 320, the system trains one or more machine learning models based on the training data set. The one or more machine learning models may be trained to generate failure predictions in respect of the OMD. For example, a first ML model may be trained to generate failure predictions for mechanical components of the OMD. A second ML model may be trained to generate failure predictions for electrical components of the OMD. A third ML model may be trained to generate failure predictions for light emitting components of the OMD. Still further ML models may be trained to generate failure predictions for other classes or types of components in an OMD. In another example, ML models may be trained to generate failure predictions for each specific component in an OMD.

At block 330, the system deploys the trained one or more ML models to one or more computing systems. In some aspects, the trained ML models may be deployed to a failure predictor executing on a same system (or cluster of systems) used to train the ML models. Alternatively, the trained ML models may be deployed to computing systems local to the OMDs, which may allow for failure predictions and preventative maintenance to be performed on OMDs that may not be connected with a central system or may have intermittent connectivity with a central system.

Figure 4:
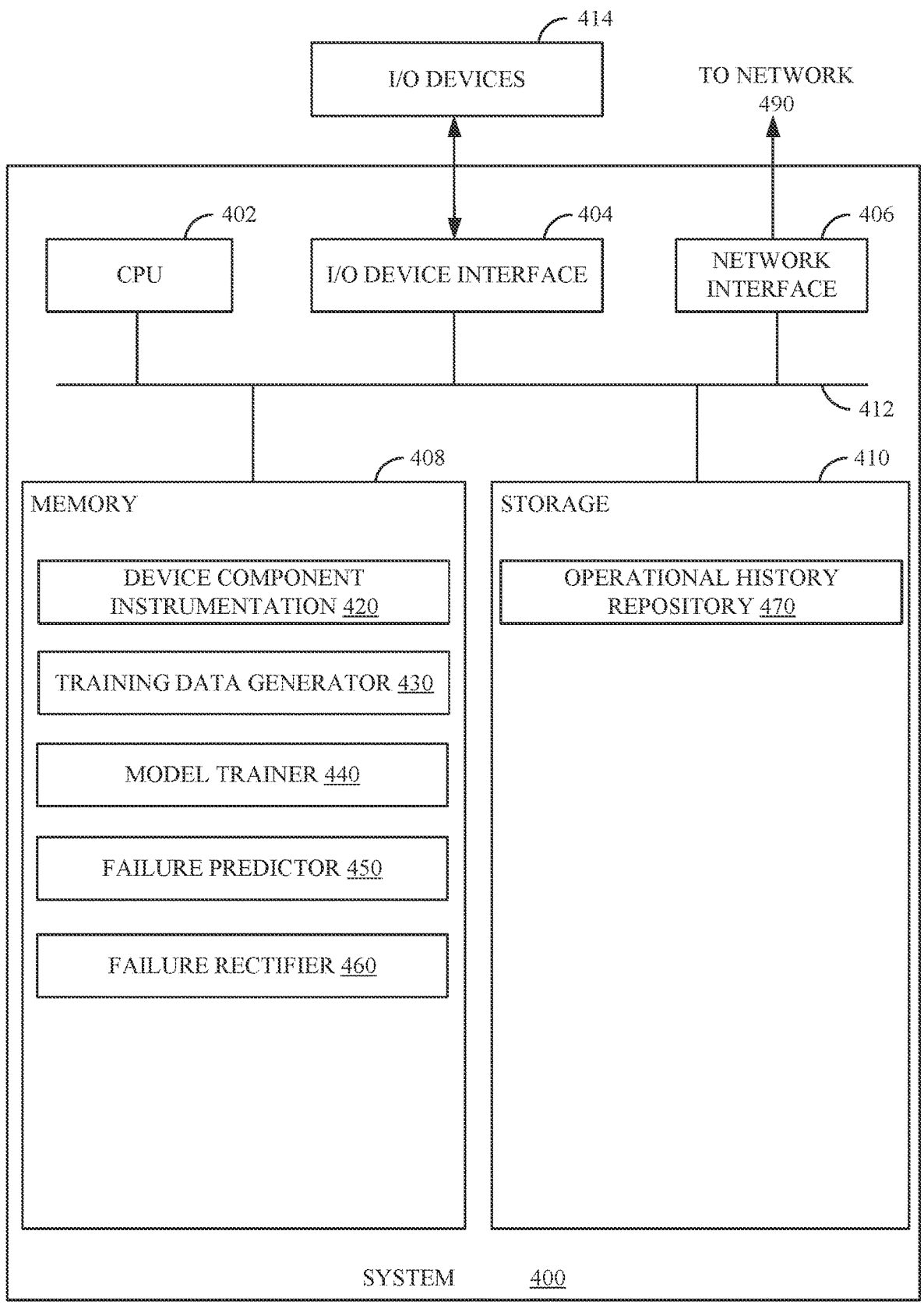
FIG. 4 illustrates an example system on which embodiments of the present disclosure can be performed.

Example System for Performing Preventative
Maintenance on Ophthalmic Medical Devices
Based on Predictive Modeling FIG. 4 illustrates an example system 400 that uses machine learning models to aid in performing surgical ophthalmic procedures, such as cataract surgeries. For example, system 400 may correspond to one or more of the measurement devices 110, server 120, and/or user console 130 illustrated in FIG. 1.

As shown, system 400 includes a central processing unit (CPU) 402, one or more I/O device interfaces 404 that may allow for the connection of various I/O devices 414 (e.g., keyboards, displays, mouse devices, pen input, etc.) to the system 400, network interface 406 through which system 400 is connected to network 490 (which may be a local network, an intranet, the internet, or any other group of computing devices communicatively connected to each other), a memory 408, storage 410, and an interconnect 412.

CPU 402 may retrieve and execute programming instructions stored in the memory 408. Similarly, the CPU 402 may retrieve and store application data residing in the memory 408. The interconnect 412 transmits programming instructions and application data, among the CPU 402, I/O device interface 404, network interface 406, memory 408, and storage 410.

CPU 402 is included to be representative of a single CPU, multiple CPUs, a single CPU having multiple processing cores, and the like.

Memory 408 is representative of a volatile memory, such as a random access memory, and/or a nonvolatile memory, such as nonvolatile random access memory, phase change random access memory, or the like. As shown, memory 408 includes device component instrumentation software 420, TDG 430, model trainer 440, failure predictor 450, failure rectifier 460, and operational history repository 470. Device component instrumentation software 420 generally interfaces with sensors and other metrology devices in an OMD to obtain measurements of various operational parameters for components of the OMD, including, but not limited to, mechanical components, electrical components, and/or optical components. The operational parameter measurements obtained by device component instrumentation software 420 generally includes various parameters that may be predictive of whether a component of the OMD is failing or likely to fail and, if so, when such failure is likely to occur.

TDG 430 generally uses the information obtained from device component instrumentation software 420 to generate training data sets used by model trainer 440 to train one or more ML models to predict a future failure of components in an OMD for use in performing preventative maintenance on the OMD. To generate the training data sets, TDG 430 can generate records associating various operational parameter measurements for components of an OMD with timing information related to the failure of the component. Records in the training data set may be persisted to operational history repository 470 in storage 410 for storage and future use in generating updated data sets to train ML models to predict a future failure of components in an OMD for use in performing preventative maintenance on the OMD.

Model trainer 440 generally trains the one or more ML models used by failure predictor 450 to predict a future failure of components in an OMD for use in performing preventative maintenance on the OMD. As discussed, model trainer 440 may use the training data sets generated by TDG 430 to train the ML models and may deploy the trained ML models to failure predictor 450 (or a remote system) for use.

Failure predictor 450 generally uses operational parameter measurements obtained via device component instrumentation software 420 to determine whether a component of an OMD is failing or likely to fail in the near future. If a component is failing or likely to fail (e.g., based on operational parameter measurements, calibration data, or anatomical measurements being outside of an expected range), failure predictor 450 can use the trained ML models to determine when the OMD is likely to fail. Based on the predictions, failure rectifier 460 can be used to perform further diagnostic tests on the component, push preventative maintenance code or remedial instructions to the OMD for execution, and/or disable the OMD until such time as the components that are failing or likely to fail are replaced.

Additional Considerations

The preceding description is provided to enable any person skilled in the art to practice the various embodiments described herein. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

The various illustrative logical blocks, modules and circuits described in connection with the present disclosure may be implemented or performed with a general purpose processor, a digital signal processor (DSP), an application specific integrated circuit (ASIC), a field programmable gate array (FPGA) or other programmable logic device (PLD), discrete gate or transistor logic, discrete hardware components, or any combination thereof designed to perform the functions described herein. A general-purpose processor may be a microprocessor, but in the alternative, the processor may be any commercially available processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

A processing system may be implemented with a bus architecture. The bus may include any number of interconnecting buses and bridges depending on the specific application of the processing system and the overall design constraints. The bus may link together various circuits including a processor, machine-readable media, and input/output devices, among others. A user interface (e.g., keypad, display, mouse, joystick, etc.) may also be connected to the bus. The bus may also link various other circuits such as timing sources, peripherals, voltage regulators, power management circuits, and the like, which are well known in the art, and therefore, will not be described any further. The processor may be implemented with one or more general-purpose and/or special-purpose processors. Examples include microprocessors, microcontrollers, DSP processors, and other circuitry that can execute software. Those skilled in the art will recognize how best to implement the described functionality for the processing system depending on the particular application and the overall design constraints imposed on the overall system.

If implemented in software, the functions may be stored or transmitted over as one or more instructions or code on a computer-readable medium. Software shall be construed broadly to mean instructions, data, or any combination thereof, whether referred to as software, firmware, middleware, microcode, hardware description language, or otherwise. Computer-readable media include both computer storage media and communication media, such as any medium that facilitates transfer of a computer program from one place to another. The processor may be responsible for managing the bus and general processing, including the execution of software modules stored on the computer-readable storage media. A computer-readable storage medium may be coupled to a processor such that the processor can read information from, and write information to, the storage medium. In the alternative, the storage medium may be integral to the processor. By way of example, the computer-readable media may include a transmission line, a carrier wave modulated by data, and/or a computer readable storage medium with instructions stored thereon separate from the wireless node, all of which may be accessed by the processor through the bus interface. Alternatively, or in addition, the computer-readable media, or any portion thereof, may be integrated into the processor, such as the case may be with cache and/or general register files. Examples of machine-readable storage media may include, by way of example, RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The machine-readable media may be embodied in a computer-program product.

A software module may comprise a single instruction, or many instructions, and may be distributed over several different code segments, among different programs, and across multiple storage media. The computer-readable media may comprise a number of software modules. The software modules include instructions that, when executed by an apparatus such as a processor, cause the processing system to perform various functions. The software modules may include a transmission module and a receiving module. Each software module may reside in a single storage device or be distributed across multiple storage devices. By way of example, a software module may be loaded into RAM from a hard drive when a triggering event occurs. During execution of the software module, the processor may load some of the instructions into cache to increase access speed. One or more cache lines may then be loaded into a general register file for execution by the processor. When referring to the functionality of a software module, it will be understood that such functionality is implemented by the processor when executing instructions from that software module.

The following claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112(f) unless the element is expressly recited using the phrase "means for" or, in the case of a method claim, the element is recited using the phrase "step for." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. A method for performing preventative maintenance on ophthalmic medical devices based on predictive modeling, comprising:

receiving, from an ophthalmic medical device, measurements of one or more operational parameters associated with the ophthalmic medical device;

receiving patient anatomical measurements generated by the ophthalmic medical device, the received patient anatomical measurements comprising eye tracking information including recorded movement of one or more biological eyes of one or more patients;

predicting, using one or more models, a future failure of the ophthalmic medical device, at least in part, on the received measurements of the one or more operational parameters and the received patient anatomical measurements, wherein predicting the future failure comprises determining that the recorded movement of the one or more biological eyes of the one or more patients has exceeded a threshold amount; and taking one or more actions to perform preventative maintenance on the ophthalmic medical device based on the predicted future failure of the ophthalmic medical device, the one or more actions comprising at least one of:

identifying a programmatic solution that, when executed on the ophthalmic medical device, remedies the predicted future failure of the ophthalmic medical device, and pushing the identified programmatic solution to the ophthalmic medical device to cause the ophthalmic medical device to execute the identified programmatic solution, or identifying one or more components of the ophthalmic medical device to be replaced in order to remedy the predicted future failure of the ophthalmic medical device, and causing a computing device to disable the ophthalmic medical device until the one or more identified components are replaced.

2. The method of claim 1, wherein the one or more models comprise a model defining values for the one or more operational parameters corresponding to normal operations for the ophthalmic medical device and vales for the one or more operational parameters corresponding to a failure of the ophthalmic medical device.

3. The method of claim 1, wherein the one or more models comprise one or more machine learning models trained to predict a future failure of the ophthalmic medical device based, at least in part, on the received measurements of the one or more operational parameters.

4. The method of claim 1, wherein the predicted future failure comprises at least one of:
   a likelihood of future failure of the ophthalmic medical device, or
   a time at which the ophthalmic medical device are likely to fail.

5. The method of claim 1, wherein the one or more operational parameters are associated with a component of the ophthalmic medical device, and wherein predicting the future failure of the ophthalmic medical device comprises predicting a future failure of the component or one or more other components in the ophthalmic medical device.

6. The method of claim 1, further comprising:
   receiving calibration data for the ophthalmic medical device or a component thereof, wherein predicting the future failure of the ophthalmic medical device is further based on trends exhibited in the calibration data over time.

7. The method of claim 1, further comprising:
   receiving usage pattern data for the ophthalmic medical device, wherein predicting the future failure of the ophthalmic medical device is further based on the usage pattern data.

8. The method of claim 7, wherein the usage pattern data includes information about system utilization over a plurality of time windows.

9. The method of claim 1, wherein the received patient anatomical measurements are generated by the ophthalmic medical device for a plurality of patients, and further comprising determining that performance of the ophthalmic medical device or a component thereof has degraded based on the received patient anatomical measurements, wherein predicting the future failure of the ophthalmic medical device is further based on the determination that performance of the ophthalmic medical device or the component has degraded.

10. The method of claim 9, wherein determining that performance of the ophthalmic medical device or the component has degraded comprises:
    determining, for each of the received patient anatomical measurements, whether the measurement is outside of a range of threshold values for a data point represented by the measurement; and
    determining that at least a threshold number of the received patient anatomical measurements is outside of the range of threshold values.

11. The method of claim 1, further comprising:
    determining, based on a comparison between a measured operational parameter for a component of the ophthalmic medical device and a range of values for the measured operational parameter defined as indicative of normal operations for the component, that performance of the component has degraded, wherein predicting the future failure of the ophthalmic medical device is further based on the determination that performance of the component has degraded.

12. The method of claim 1, wherein the one or more operational parameters are associated with a component of the ophthalmic medical device, and wherein the one or more actions further comprise:
    identifying one or more actions to perform using the component of the ophthalmic medical device;
    transmitting one or more instructions to the ophthalmic medical device to execute the identified one or more actions;
    receiving additional measurements of operational parameters from the ophthalmic medical device in response to transmitting the one or more instructions; and
    determining, based on the received additional measurements, one or more additional actions to execute to perform preventative maintenance on the component based on the predicted future failure.

13. The method of claim 1, wherein the one or more operational parameters are associated with a component of the ophthalmic medical device, and further comprising:
    generating an aggregated data set by aggregating the measurements of the one or more operational parameters associated with the component of the ophthalmic medical device and the predicted future failure of the ophthalmic medical device with measurements and predictions from a plurality of other ophthalmic medical devices; and
    generating, based on the aggregated data set, one or more analyses illustrating trends across a plurality of groups of ophthalmic medical devices.

14. The method of claim 1, further comprising:
    outputting, for display to a user of the ophthalmic medical device, a notification including information identifying one or more components of the ophthalmic medical device that are likely to fail, the predicted future failure, and information about the one or more actions taken to perform preventative maintenance.

15. The method of claim 1, wherein the programmatic solution causes the ophthalmic medical device to be recalibrated.

16. The method of claim 1, wherein the programmatic solution includes one or more updated calibration targets for recalibrating at least one component of the ophthalmic medical device.

17. A method for training a predictive model to predict failure events on an ophthalmic medical device, comprising:
    generating a training data set from a set of measurements of operational parameters associated with the ophthalmic medical device, wherein the training data set includes a plurality of records and each record of the plurality of records identifies:
    patient anatomical measurements generated by the ophthalmic medical device, the patient anatomical measurements comprising eye tracking information including recorded movement of one or more biological eyes of one or more patients;
    a measurement of an operational parameter,
    a time at which the operational parameter was measured, and
    a difference between the time at which the operational parameter was measured and a time at which a failure event occurred with respect to the ophthalmic medical device;
    training one or more machine learning models based on the training data set to generate one or more failure predictions in respect of the ophthalmic medical device;

deploying the trained one or more machine learning models to one or more computing systems, wherein the one or more computing systems predict, using the trained one or more machine learning models, a future failure of at least one ophthalmic medical device, at least in part, on a set of measurements of the operational parameter and the patient anatomical measurements, wherein predicting the future failure comprises determining that the recorded movement of the one or more biological eyes of the one or more patients has exceeded a threshold amount; and taking one or more actions to perform preventative maintenance on the at least one ophthalmic medical device based on the predicted future failure of the at least one ophthalmic medical device, the one or more actions comprising at least one of:
identifying a programmatic solution that, when executed on the at least one ophthalmic medical device, remedies the predicted future failure of the at least one ophthalmic medical device, and pushing the identified programmatic solution to the at least one ophthalmic medical device to cause the at least one ophthalmic medical device to execute the identified programmatic solution, or
identifying one or more components of the at least one ophthalmic medical device to be replaced in order to remedy the predicted future failure of the at least one ophthalmic medical device, and causing a computing device to disable the at least one ophthalmic medical device until the one or more identified components are replaced.

18. The method of claim 17, wherein the measurements of operational parameters comprise power measurements for an electrical component in the ophthalmic medical device.

19. The method of claim 17, wherein the measurements of operational parameters comprise usage information over a time window.

20. The method of claim 17, wherein training the one or more machine learning models comprises training a multi-output machine learning model that generates, for the one or more measurements of operational parameters, an output identifying a prediction of whether the ophthalmic medical device is likely to fail within a time period from when the prediction is made and a remaining time before a failure event occurs on the ophthalmic medical device.

21. The method of claim 17, wherein training the one or more machine learning models comprises training a first machine learning model that generates a prediction of whether the ophthalmic medical device is likely to fail within a time period from when the prediction is made and a second machine learning model that predicts a remaining amount of time before a failure event occurs on the ophthalmic medical device.

22. The method of claim 17, wherein deploying the trained one or more machine learning models to one or more computing systems comprises deploying the trained one or more machine learning models to a computer integral with the ophthalmic medical device.

23. The method of claim 17, wherein deploying the trained one or more machine learning models to one or more computing systems comprises deploying the trained one or more machine learning models to a remote server with which one or more ophthalmic medical devices are communicatively coupled.

24. A method for performing preventative maintenance on ophthalmic surgical devices based on preventative modeling, comprising:
generating a training data set from a set of measurements of operational parameters associated with an ophthalmic medical device, wherein the training data set includes a plurality of records and each record of the plurality of records identifies:
a measurement of an operational parameter,
a time at which the operational parameter was measured, and
a difference between the time at which the operational parameter was measured and a time at which a failure event occurred with respect to the ophthalmic medical device;
training one or more machine learning models based on the training data set to generate one or more failure predictions in respect of the ophthalmic medical device;
receiving patient anatomical measurements generated by the ophthalmic medical device, the received patient anatomical measurements comprising eye tracking information including recorded movement of one or more biological eyes of one or more patients;
receiving, from the ophthalmic medical device, measurements of one or more operational parameters associated with the ophthalmic medical device and the received patient anatomical measurements;
predicting, using the one or more trained machine learning models, a future failure of the ophthalmic medical device based, at least in part, on the received measurements of the one or more operational parameters and the received patient anatomical measurements, wherein predicting the future failure comprises determining that the recorded movement of the one or more biological eyes of the one or more patients has exceeded a threshold amount; and
taking one or more actions to perform preventative maintenance on the ophthalmic medical device based on the predicted future failure of the ophthalmic medical device, the one or more actions comprising at least one of:
identifying a programmatic solution that, when executed on the ophthalmic medical device, remedies the predicted future failure of the ophthalmic medical device, and pushing the identified programmatic solution to the ophthalmic medical device to cause the ophthalmic medical device to execute the identified programmatic solution, or
identifying one or more components of the ophthalmic medical device to be replaced in order to remedy the predicted future failure of the ophthalmic medical device, and causing a computing device to disable the ophthalmic medical device until the one or more identified components are replaced.

* * * * *